United States Patent [19]
Pak et al.

[11] Patent Number: 5,381,797
[45] Date of Patent: Jan. 17, 1995

[54] PULSE DIAGNOSTIC DEVICE AND METHOD OF MEASURING A PULSE WAVE USING THIS DEVICE

[76] Inventors: Song C. Pak, Snegovaya st., 125-724; Vladimir V. Goltcov, Internationalnaya st., 63-9, both of Vladivostok, 690000; Alexander Y. Kryssov, Plescheeva st., 1-63, Moscow, 127560; Igor I. Emelianov; Igor P. Emellianov, both of Kirova st., 7/3-79, Yakutsk, 677007; Evgeny E. Kotekin, Melnikayte st., 135-486, Tyumen, 625045, all of Russian Federation

[21] Appl. No.: 53,609

[22] Filed: Apr. 26, 1993

[30] Foreign Application Priority Data

Mar. 26, 1993 [SU] U.S.S.R. ............... 5029329

[51] Int. Cl.⁶ .............................. A61B 5/0245
[52] U.S. Cl. ........................ 128/687; 128/688
[58] Field of Search .................. 128/687–690, 128/672, 677, 678

[56] References Cited

U.S. PATENT DOCUMENTS

| | | | |
|---|---|---|---|
| 3,318,303 | 5/1967 | Hammacher | 128/687 X |
| 3,361,128 | 1/1968 | Colman | 128/687 |

*Primary Examiner*—Angela D. Sykes
*Attorney, Agent, or Firm*—Marger Johnson McCollom & Stolowitz

[57] ABSTRACT

A pulse diagnostic device has a pulse wave sensor, a pulse wave signal processing unit and a register—all connected in series. The sensor is provided with means for correcting its amplitude-frequency response to obtain a prescribed shape of the pulse wave signal. The processing unit has an amplifier, an analog-to-digital converter and an analyzer all connected in series for analyzing of the pulse wave signal shape according to prescribed parameters. The method of measuring a pulse wave using the pulse diagnostic device resides in the fact that the sensor is pressed to the wrist in the Cyn, Gyan and Chi points, regulating the force of pressure; in so doing, one creates a pressure force by hand and regulates the position of the sensor corresponding to the measurement of a surface and/or deep or full pulse, until the first maximum value of the maximum amplitude of a signal appears to be visually received in the register.

9 Claims, 5 Drawing Sheets

PULSE DIAGNOSTIC DEVICE AND METHOD OF MEASURING A PULSE WAVE USING THIS DEVICE

FIELD OF THE ART

The invention relates to medicine and, more specifically, to the definition, measurement or registration for diagnostic purposes, and pertains to a pulse diagnostic device and a method of measuring the pulse wave using this device.

The invention can be used to advantage in clinical practice for the diagnostics and physiological control of the human health.

BACKGROUND OF THE INVENTION

The development of modern methods of clinical diagnostics and physiological control of the condition of human health, combining in itself express-effect, simplicity and high self-descriptiveness is one of the typical problems facing contemporary physiology, medicine and medical instrument making.

Present day Western medicine makes use of diversified instrumental methods involving tonometers, cardiographs, sphygmographs, plethysmographs and the like to conduct a special study of a particular feature of the cardiovascular system functioning, namely, evaluation or pressure changes in the blood flow, the condition of vessels' walls, and various hemodynamic parameters.

Oriental medicine, in turn, regards the pulse study as a universal method of diagnostics. Pulse diagnostics has been considered as the "kernel" of Oriental medicine and represented a sophisticated and subtle method for assessing the functional condition of practically every organ and system in the human organism. Figuratively speaking, the radial artery in the wrist zone is viewed by an oriental doctor as the focus and resonator where various physiological processes in the organism manifest themselves most vividly. The entire complex of sensations when palpating the pulse carries information about the condition of functional systems, the type and character of disorders, and the prognosis as regards the course of a disease.

Until recently, however, mastering the technique of pulse diagnostics has been fairly difficult owing to the duration (15 to 20 years) and difficulty of instruction, requiring a pulse diagnostician to have specially sensitive fingers, as well as the impossibility of acquiring objective information received from the pulse for collation and analysis.

In this connection, it has become necessary to develop devices permitting pulse diagnostics to be made more objective and teaching pulse diagnostics methods to be made easier.

One of the basic elements of pulse diagnostic devices is a pulse wave sensor, serving to convert different kinds of energy, e.g., mechanical energy of a pulse beat to an electrical signal. All major types of pulse wave sensors, namely, capacitive, tensometric, optical, piezoelectric, transform mechanical oscillations of the radial artery, which are the basic carrier of information, to an electric signal.

In Oriental medicine the pulse was studied in several positions, namely, in the wrist zone, on the radial and ulnar arteries, in the region of malleoluses, in carotids, in the lubital region, etc. But it is the wrist zone on the carotid in the area of the styloid process that was considered the main place for diagnostics. This place was regarded as the one connecting all canals and vessels of the body. But arranged close to the carotid are the venous and lymphatic vessels, the nerve trunk, as well as the meridian of the lungs, according to the teaching of Oriental medicine about the meridians. The condition of adjacent tissues also affects the pulse perception. Besides, according to the contemporary biophysics, the wave comprises the processes different by nature, namely, the movement of blood along a vessel, mechanical peristalsis wave running along the vessel, a sound wave formed from an impact during a systolic blood ejection from the heart to the blood channel and, in the final analysis, an electromagnetic wave. Each of these processes has its flow speed and its own character of action. Thus, in the place of the pulse wave collection there is formed a complex conglomerate of various processes both in the carotid per se and the effects on the part of adjacent vessels, namely, venous, lymphatic and nerve trunks. An experienced pulse diagnostician perceives not only general parameters in the form of frequency, strength and rhythmicity, fullness of the pulse, but also "burning", "prick", "hardening", "vibration" and the like, characterizing, in addition to the level and character of functional processes, the presence of inflammation, spasms or lithogeny, respectively. Hence, the physician's fingers, trained over dozens of years, serving as supersensitive biological sensors, perceive not only mechanical oscillations of the wall of the radial artery stipulated by its deformation caused by the blood pressure pulse, but also other finer and more subtle wave processes.

In this connection, there arises a problem of measuring the pulse wave, conditioned by the necessity of obtaining complete information about the processes in the section of the radial artery in the place of measurement, and correct interpretation of a pulse wave signal to make the diagnosis. The aforementioned sensors of the pulse wave have their own technical characteristics and, in particular, an amplitude-frequency response, stipulating the shape of a pulse wave signal. However, the amplitude-frequency responses of these sensors are such that as the pulse wave is measured, the pulse wave signal does not fully reflect all the processes at the section of measurement.

Closest to the invention claimed is a pulse-diagnostic device (U.S. Pat. No. 4,066,066), comprising, at least, one pulse wave sensor mounted on the inside of the wrist in the Cyn, Gyan and Chi points reflecting the condition of the internal organs and systems, a unit for processing the pulse wave signals, which processes n-sets of the pulse wave signal connected to the pulse wave sensor, and a register whose input is connected to the output of the pulse wave signal processing unit.

In said pulse diagnostic device the pulse waves are measured simultaneously by three pulse wave sensors secured on the patient's wrists. The force of pressing the pulse wave sensors is regulated by means of a vacuum cuff encompassing the wrist at the section of the pulse wave sensor arrangement.

An amplifier is used as a unit to process the pulse wave signals. From each pulse wave sensor an amplified signal enters the ammeter end/or register.

In U.S. Pat. No. 4,066,066, piezoelectric microphones serve as pulse wave sensors converting mechanical oscillations stipulated mostly by the deformation of the radial artery at the sections of measurement, caused by the blood pressure pulse. However, as was noted above, the pulse wave is a far more complicated phenomenon than only mechanical oscillations of the radial artery: it is a combination of all wave processes from slow, namely, the blood flow and the peristaltic wave, up to rapid, including sonic and electromagnetic ones. Thus, as the pulse wave is measured, the piezoelectric microphone perceives only part of the information about the pulse which is due to the amplitude-frequency response of the piezoelectric microphone and this is reflected also in the shape of the pulse wave signal.

The pulse-diagnostic device being described is a sphygmograph intended to be used in practice based on the methods of Chinese medicine. Analysis of the pulse wave signals, which in actual fact are only amplified and then registered, is made by the doctor visually. The analysis is carried out with due regard for the amplitude (beat strength) characterizing the pulse as pulses magnus or pulses parvus, for the frequency of beats, characterizing the pulse as swift of slow pulse, and for rhythmicity, characterizing the pulse as rapid (non-rhythmic) or equal (rhythmic).

The pulse is regarded as a single information field and, depending on the depth of maximum amplitude, can be surface, i.e., "bright", "active", deep, i.e., "small", "weak", perceived only upon fully pressing the wrist, and intermediate between the first two.

The Cyn, Gyan, Chi points in which measurement is taken from the radial artery on the wrist, show the character of disturbance, namely, in the Cyn region—from head to chest, in the Gyan region—from the diaphragm to the navel, and in the Chi region—from the navel to the feet.

The pulses are referenced to the specific organs by virtue of empirically derived criteria. For instance, as to the heart and lungs, referred to the Yang point, a prolonged and active is referred to the heart, and brief and slow pulse—to the lungs.

For the liver and kidneys related to the Yin point, a long pulse relates to the kidneys and a short and soft pulse—to the liver. It is said that the spleen pulse occupies an intermediate position and is diagnosed with difficulty.

Solution of the problem of locating the place of a disease is interpreted as follows: a rapid pulse corresponds to the Yan region (six hollow organs), and a slow pulse—to the Yin region (five dense organs).

Using the above-identified criteria, one singles out the basic types of pathological pulses in the classical Chinese medicine: a tense pulse, large pulse, small pulse: high spirit, but little blood, small pulse: "little spirit and blood", abrupt pulse: "Yah thrives, Yin is absent", soft pulse: "Yin thrives, Yan is absent".

In view of the foregoing, one can draw the following conclusions. In the said method the surface and deep pulses, taken in one pulse position, are not differentiated as the pulses related to different organs, namely, hollow (Yan) and dense (Yin), respectively. The pulse wave is analyzed as regards the strength, rate and rhythmicity or beats, and the shape of the pulse wave signal is not analyzed.

The above-described interpretation of pulses performed by a doctor visually rules out automation in obtaining the diagnostic conclusions and collation of the data obtained, as well as it makes the diagnosis more subjective and the training of a doctor becomes difficult.

The method of measuring a pulse wave by means of said pulse diagnostic device consists in the fact that the pulse wave sensor is pressed to the wrists in the Cyn, Gyan, Chi points, regulating the pressure force with the aid of a vacuum cuff. Since the pulse wave is measured in said three points at a time and the force of pressing the piezoelectric microphones to the patient's wrist is set practically equal, it is fairly probable that the measurement in an adjacent point affects that of a pulse wave in each of said points, thus impairing the authenticity of information. Besides, as the pulse wave is measured simultaneously in three points, it is impossible to control the position of piezoelectric microphones to obtain reliable information about the surface and deep pulses.

BRIEF DESCRIPTION OF THE INVENTION

It is an object of the invention to provide a pulse diagnostic device making pulse diagnostics more objective due to obtaining a similar standard shape of the pulse wave signal for twelve organs and systems and disclosing the parameters of the pulse wave signal which enables one to provide the method of clinical diagnostics and physiological control of patients' health.

It is another object of the invention to automate analysis of the shape of the pulse wave signal by virtue of the parameters revealed, thus permitting the analysis be markedly speeded up, the accuracy of analysis results be enhanced and a complex procedure of making the diagnosis be simplified.

One of the objects of the invention is to provide a method of measuring the pulse wave by means of a pulse diagnostic device enabling one to correct the position of the pulse wave sensor during measurement to obtain a prescribed shape of the pulse wave which additionally reduces the time of examining patients and ensures authenticity of the measurement of a pulse wave in each position.

The objects set forth are attained due to the fact that the pulse diagnostic device, according to the invention, comprises, at least, one pulse wave sensor mounted on the inside of wrists in the Cyn, Gyan and Chi points, reflecting the condition of internal organs and systems, convening the pulse wave into a pulse wave signal; means to correct the amplitude-frequency response of said pulse wave sensor to obtain a prescribed shape of the pulse wave signal; a unit for processing the pulse wave signals which process the group of sets of the pulse wave signal; having an input and output connected by said input to said pulse wave sensor and comprising: an amplifier having an input serving as said input of said pulse wave signal processing unit, and an output; an analog-to-digital converter having an input and an output connected by said input to said output of said amplifier; an analyzer of the pulse wave signal shape, that analyzes according to prescribed parameters, having an input connected to said output of said analog-to-digital converter and an output serving as said output of said pulse wave signal processing unit; a register having the first input connected to said output of said pulse wave signal processing unit.

It is expedient that said means for correcting the amplitude-frequency response of said pulse wave sensor be made so that each set of the pulse wave signal contain the first, second, third, forth and fifth characteristic sinusoidal half-waves following one after another, in so doing, the first characteristic half-wave represents a positive characteristic half-wave, the second characteristic half-wave—represents a negative characteristic half-wave whose amplitude would be essentially equal to that of the first characteristic half-wave—positive characteristic half-waves of basically the same amplitude which would be less than that of the first characteristic half-wave, and the fifth characteristic half-wave whose amplitude would be equal or less than the amplitude of the third or fourth characteristic half-waves and the duration of which would essentially equal the total duration of the first, second third and fourth characteristic half-waves.

It is useful that the pulse diagnostic device should comprise: a microphone serving as said pulse wave sensor; a chamber serving as said means for correcting the amplitude-frequency response of said pulse wave sensor arranged in front of said microphone; the working medium filling said chamber.

It is advantageous that said chamber should be open from the side of the entry of an acoustic wave, in so doing, air should serve as said working medium.

It is effective that said analyzer of the shape of the pulse wave signal according to prescribed parameters should comprise: a memory unit having an input serving as said input of said analyzer, and an output; a unit for separation of an individual complex with the maximum energy and disclosing therein of characteristic half-waves having an input and output, connected by said input to said output of said memory unit; a calculator of parameters designed to calculate maximum amplitudes and lengths of the first and second half-waves, relationships of the lengths of the set and the fifth characteristic half-wave having the inout and output connected by said inout to said output of said unit of separation of the individual set; a comparator unit having the first and second inputs and an output connected by the first input to said output of said calculator of parameters; a set-point device of standard values of said parameters, which has an output connected by the second input of said comparator unit, whose said output serves as said output of said analyzer.

It is reasonable that the pulse-diagnostic device should comprise: said register having the second input; said amplifier of said processing unit, connected by said output to the second input of said register registering a group of sets of the pulse wave signal.

The object set forth are attained also by the fact that the method for measuring the pulse wave by means of the pulse diagnostic device, comprising a pulse wave sensor, according to the invention, comprises the following operations: pressing the pulse wave sensor to the wrists in the Cyn, Gyan and Chi points, reflecting the condition of the internal organs and systems effected with a force created by hand; regulation of the force of said pressure to install the pulse wave sensor in the positions corresponding to the measurement of the surface and/or deep pulses; said regulation effected until the first maximum value of the maximum amplitude of the pulse wave signal which is visually perceived in the register.

The pulse diagnostic device of the invention allows for making pulse diagnostics more objective by way of using a pulse wave sensor with means to correct the amplitude-frequency response, ensuring while measuring the pulse wave of twelve organs and systems, the provision of an identical standard shape of the pulse wave signal, also thanks to using the analyzer of the pulse wave signal shape according to the prescribed parameters.

The above-identified shape of the pulse wave signal, being the sequence of characteristic sinusoidal half-waves downgoing in amplitude and all of them, except the second, are positive half-waves, is most informative which gives with its changes a subtle picture of the functional condition of organs and systems in the patient's organism.

The disclosure of a number of standard deviations from the standard shape of the curve showing the presence of different functional and organic pathologies and present in any of the twelve pulse waves when the organ is sick with which this pulse wave is related to, makes possible to create a language common for all the twelve pulses, describing the parameters of a pulse wave signal and parameters of deviations. Automation of the analysis of the shape of the pulse wave signal according to these parameters enables one to markedly speed up the analysis and enhance the accuracy of results. The complicated procedure of making the diagnosis and training of the doctor-pulse diagnostician is simplified.

Possibility of a visual perception of the shape of a pulse wave signal, alongside the possibility of correcting the position of the pulse wave sensor during measurement, effected directly by the pulse diagnostician allow of additionally reducing the time of patient's examination, establishing the reliability of measurement of the pulse wave in each position by the shape of the pulse wave signal.

BRIEF DESCRIPTION OF THE DRAWINGS

The invention will become more apparent by the description of specific embodiments thereof and accompanying drawings in which:

FIG. 6 (a, b, c, d, e, f) shows time diagrams of the pulse wave signals, illustrating the block-diagrams of the algorithms of the unit for separating the individual set with the maximum energy and the calculator;

DETAILED DESCRIPTION OF THE INVENTION

Figure 1:
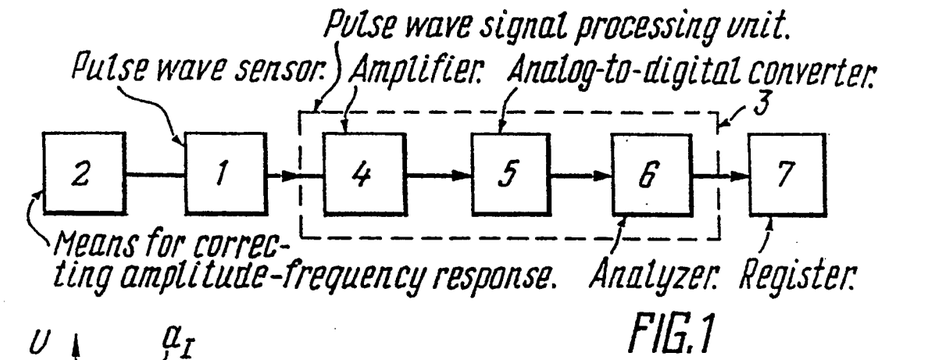
FIG. 1 shows a functional block-diagram of a pulse diagnostic device.

The pulse diagnostic device has at least one sensor 1 (FIG. 1) of a pulse wave, mounted on the inside of the wrists in the Cyn, Gyan and Chi points, reflecting the condition of internal organs and systems of the patient, in two positions, namely, in the position corresponding to measurement of the surface pulse in the point, and in the position corresponding to measurement of a deep pulse. It is possible to measure the pulse waves in said points using one pulse wave sensor, as well as simultaneously measure pulse waves in two points in different hands using two pulse wave sensors. The pulse wave sensor 1 is furnished with means 2 for correcting its amplitude-frequency response to obtain a prescribed shape of a pulse wave signal. The output of the pulse wave sensor 1 is connected to the input of the unit 3 for processing pulse wave signals, which processes the group of sets of the pulse wave signal. In the processing unit 3 the pulse wave signal enters the input of the amplifier 4, whose output is connected to the input of the analog-to digital converter 5 by the output connected to the input of the pulse wave signal shape analyzer 6. The output of the analyzer 6 is connected to the first input of the register 7.

Figure 2:
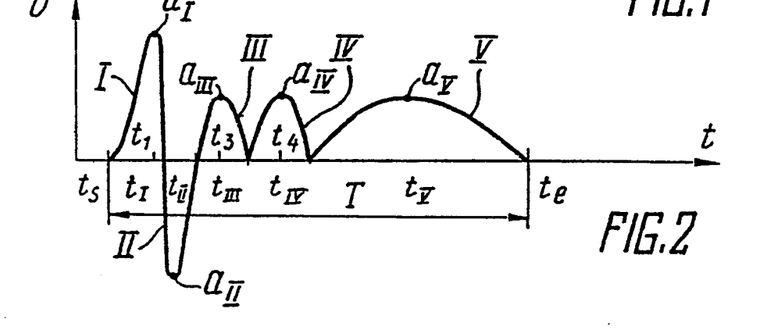
FIG. 2 illustrates a time diagram of the pulse wave signal having a standard shape.

FIG. 2 shows a standard shape pulse wave signal where the x-axis represents time and the y-axis represents voltage. The means 2 for correcting the amplitude-frequency response of the pulse wave sensor is made so that each set of the pulse wave signal contains five characteristic sinusoidal half-waves, one after another. The first characteristic half-wave I (FIG. 2) represents a positive characteristic half-wave, the second characteristic half-wave II—a negative characteristic half-wave whose amplitude is actually equal to that of the first characteristic half-wave I. The third III and Fourth IV characteristic half-waves are positive characteristic half-waves of basically similar amplitude which is less than that of the first characteristic half-wave I. The fifth characteristic half-wave V is a positive characteristic half-wave whose amplitude is equal or less than that of the third III or fourth IV characteristic half-waves and whose length is essentially equal to the total length of the first, second, third and fourth characteristic half-waves I, II, III and IV.

The described pulse wave signal shape is a standard one, characteristic of a healthy patient. In so doing, all the pulse wave signals received when measuring the pulse wave in twelve positions, have the same shape. Said shape of the pulse wave signal is established empirically and gives a fairly subtle picture by its changes of the functional condition of the patient's organs and systems, trapping such subtleties which are probably not easily accessible even to experienced pulse diagnosticians.

When using a microphone as the pulse wave sensor 1 (FIG. 1), the means 2 (FIG. 3) for correcting the amplitude-frequency response is made in the form of a chamber arranged in front of the microphone and filled with a working medium. The choice of a microphone is stipulated by the conceptions of Chinese medicine maintaining that the pulse is the speech of the human organism giving a comprehensive account of all its functional processes.

Figure 3:
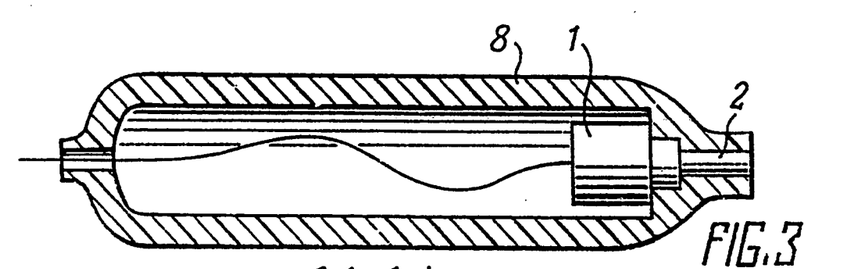
FIG. 3 shows the general view of the pulse wave sensor with means for correcting the amplitude-frequency response (longitudinal section)

One of the embodiment variants of the chamber is the one open from the side of the application of an acoustic wave. Air serves as the working medium in this chamber. The shape and size of the chamber are selected empirically, proceeding from said shape of the pulse wave signal. In actual fact the chamber is an acoustic filter with a bandwidth within 5 to 135 Hz.

It is expedient that an electret microphone having high sensitivity be used as the pulse wave sensor 1.

Structurally, the microphone is accommodated in a body 8, part of the body 8 serving as a chamber.

A pulse wave signal shape analyzer 6 (FIG. 4) according to the prescribed parameters has a memory unit 9 to the input of which a signal is applied from the output of an analog-to-digital converter 5. The output of the memory unit 9 is connected to the input of a unit 10 for singling out a separate set with the maximum energy and revealing therein of characteristic half-waves, whose output is connected to the input of a calculator 11 of parameters. The calculator 11 is designed to calculate the maximum amplitudes $a_I$, $a_{II}$ and lengths $t_I$, $t_{II}$ of the first I and second II characteristic half-waves, $a_{IV}/a_{III}$ relationship of the maximum amplitudes of the fourth IV and third III characteristic half-waves and the $T/t_V$ relationship between the lengths of the set and the fifth characteristic half-wave V. The output of the parameter calculator 11 is connected to the first input of a comparator unit 12, a set-point device 13 of standard values of parameters being connected to the second input of said comparator unit.

Figure 4:
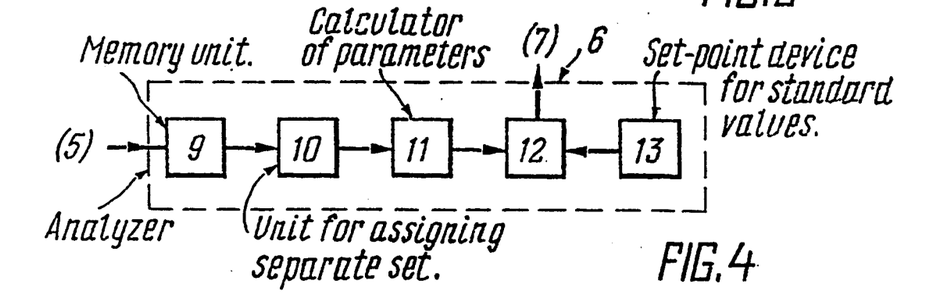
FIG. 4 shows the functional block-diagram of the analyzer of the shape of the pulse wave signal according to the prescribed parameters.

A computer, operating according to a special program of mathematical processing, is used as the analyzer 6.

The pulse diagnostic device operates as follows. The pulse wave sensor 1 (FIG. 1) is arranged consecutively in the Cyn, Gyan and Chi points on each wrist, in each point first in the position corresponding to measurement of a surface pulse and then a deep one which is necessary for obtaining information about all organs and systems of the patient. The pulse wave being measured passes through the means 2 (FIG. 3) for correcting the amplitude-frequency response—the chamber of the sensor 1 and is converted by the microphone into an electric signal. In actual fact, an acoustic low-frequency signal enters the microphone in a range stipulated by the chamber parameters which can be verified to obtain a most informative signal. A pulse wave signal, comprising five characteristic half-waves I-V (FIG. 2) enters the input of the processing unit 3 (FIG. 1), wherein it is first amplified by the amplifier 4 and then is converted by the analog-to-digital converter 5, whereupon, it enters the input of the analyzer 6.

Figure 5:
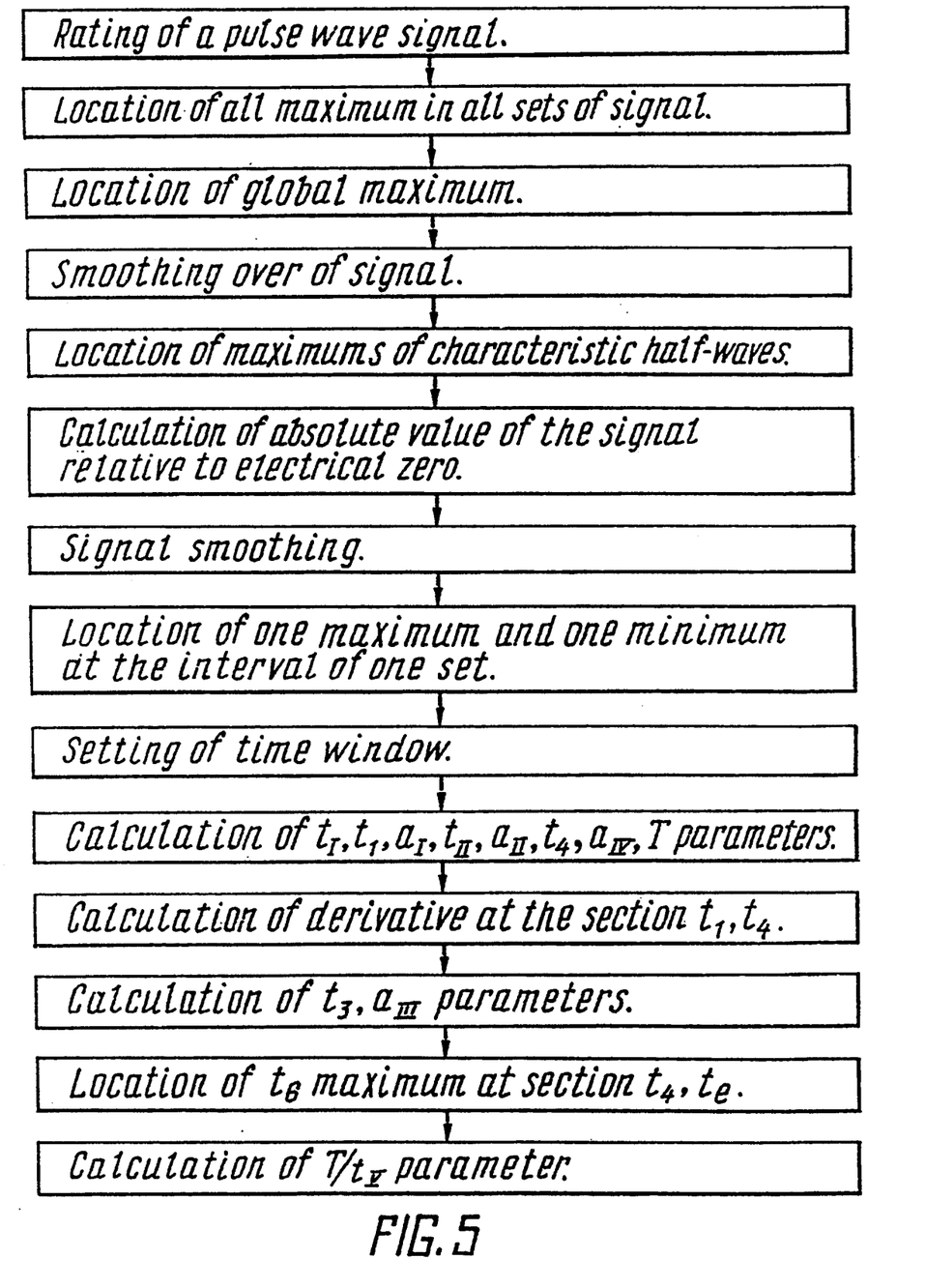
FIG. 5 shows the block-diagram of the algorithms of the unit for separating an individual set with the maximum energy and a calculator incorporated in the analyzer of the pulse wave signal shape according to the prescribed parameters.
Figures 6A, 6B, 6C, 6D:
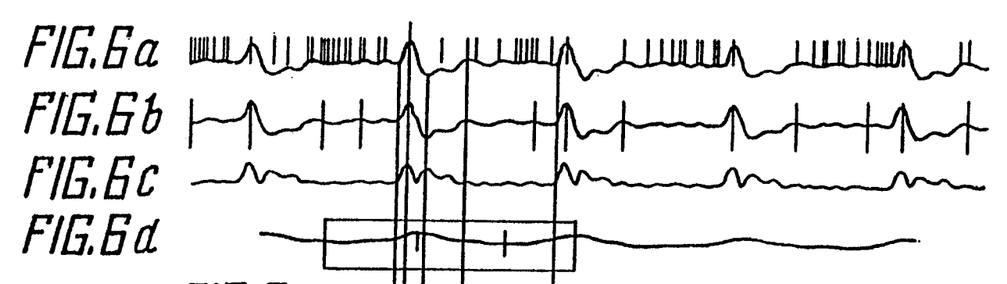
Figures 6E, 6F:
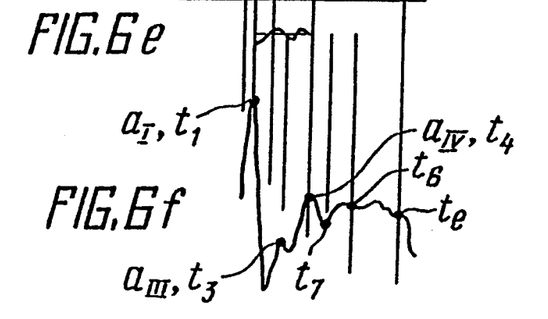

The pulse wave signal shape is analyzed as follows according to the prescribed parameters. First, the pulse wave signal is stored in the memory unit 9 (FIG. 4), thereupon, it enters the input of the unit 10 for assigning a separate set with the maximum energy and revealing therein of characteristic half-waves. The algorithm of processing the pulse wave signal in the assigning unit 10 represented in FIG. 5, consists of a system of consecutively executed elementary conversions which reside in the following. First, the pulse wave signal is normalized by dividing into the maximum amplitude, then all maximums marked by vertical lines are localized in all sets of the pulse wave signal, thereupon,—global maximum is found. This stage of conversions is illustrated by the time diagram "a" represented in FIG. 6, in which the pulse wave signal amplitude is plotted on the ordinate.

Then, the pulse wave signal is smoothed over three points (filtration), whereupon, fluctuations fully disappear and the maximums of characteristic half-waves are found by means of a logical circuit of the form: $x_i < x_{i+1} < x_{i+2}$ ... along the contour of a signal. This stage of conversions is illustrated by a time diagram "b", FIG. 6.

Then, the absolute value of a signal (a curve given in the "b" diagram) is calculated relative to the electrical zero (modulation). The absolute value of the curve is given in the time diagram "c", FIG. 6.

Thereupon, the pulse wave signal is smoothed over 21 points to locate one set of one maximum (short vertical line). Then, a time window is set, beyond which there cannot be above-identified parameters of the set. This stage of conversions is illustrated by the time diagram "d", FIG. 6 and completes the sequence of conversions as illustrated by the time diagram "d", FIG. 6 and completes the sequence of conversions in the unit 10 (FIG. 4) of assigning a separate set.

Upon setting the time window, the parameters $t_I$, $t_1$, $a_I$, $t_{II}$, $a_{II}$, $t_4$, $a_{IV}$, as well as parameters $t_s$, $t_e$, corresponding to the beginning and end of the set. Thereupon, the derivative is calculated at the $t_1$, section (FIG. 2), $t_4$, illustrated by the "e" time diagram, FIG. 6 and parameters $t_3$, $a_{III}$ are calculated.

Presented in the "f" time diagram is the initial curve of the pulse wave signal with 5× magnification and limitation as regards the assigned set, in which the maximum $t_6$ is defined in section $t_4$, $t_6$. Thereafter, the parameter T/tV is calculated, i.e., $t_e - t_s/t_e - t_7$.

All the above-identified parameters are calculated in the calculator 11 (FIG. 4). The signals carrying information about the numerical values of parameters enter the input of the comparator unit 12, in which these are compared with the standard values recorded in the set-point device 13. The result of the comparison of parameters is reflected in the register 7, i.e., the monitor display.

As noted above, it has been established that given a healthy organism, the pulses in all positions characterizing different organs and systems have a similar shape, giving a fairly subtle picture by its changes of the functional condition of organs and systems, and the parameters characterizing the shape. Thus, a universal approach to the diagnostics of the integral organism is evolved from the standpoint of functioning organs. The shape of the pulse wave signal in a healthy organism and the character of variation of the characteristic half-waves of the signal have been experimentally established, given a certain functional change in any of the 12 organs and systems in keeping with the positions of pulse diagnostics.

The parameters evolved in the pulse wave signal curve shown in FIG. 2 carry the following information:

$a_I$, the maximum amplitude of the first characterizing half-wave I corresponds to the level of the system functional activity;

$a_{II}$, the maximum amplitude of the second characterizing half-wave II corresponds to the level of the system resistance, the organ potency;

$a_{III}$, the maximum amplitude of the third characterizing half-wave III corresponds to the level of constructive (recovering) process inside the organ;

$a_{IV}$, the maximum amplitude of the fourth characteristic half-wave IV corresponds to the level of destructive processes inside the organ (destructive factor);

$a_{IV}/a_{III}$, the characteristic of the balance inside the organ;

T/$t_V$, intensity of the functioning process;

$t_I$, $t_{II}$, the characteristics of the psychic effect on the organ functioning.

For instance, if the organs or systems fail to function normally, one parameter or another of the curve in any combination alters, respectively, on the pulse wave signal curve obtained. The analyzer 6 (FIG. 4) calculates the values of all parameters, involving their evaluation with due regard for rates evolved through research which are established for each parameter.

Thus, the numerical values of the pulse wave signal parameters obtained on the analyzer 6 are compared with their standard values and the value of deviation is registered on the monitor display to enable one to make pulse diagnostics more objective, to speed up the analysis and enhance the accuracy of analysis results. A complicated procedure of making the diagnosis is simplified.

Figure 7:
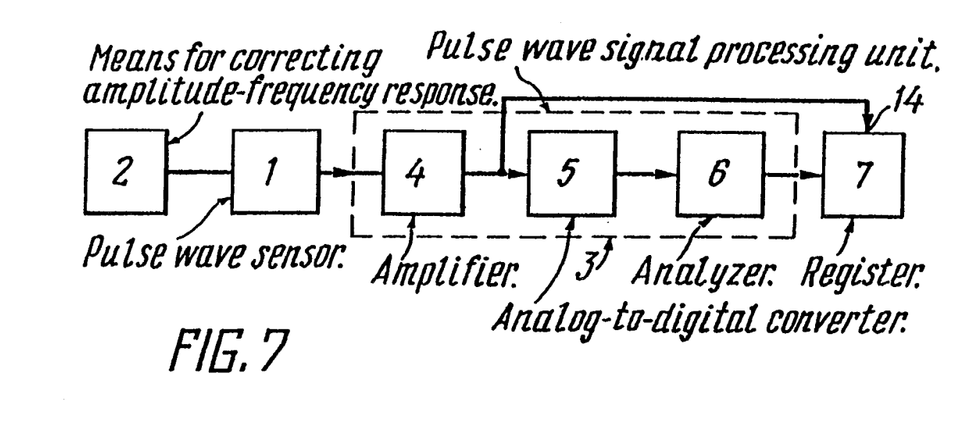
FIG. 7 is the same as in FIG. 1, with an additional electric connection of the pulse wave sensor with the register, bypassing the pulse wave signal shape analyzer.

In order to correct the position of the pulse wave in each of the positions in the Cyn, Gyan and Chi points in the patient's wrists, the output of the amplifier 4 (FIG. 7) in the pulse diagnostic device is connected to another input 14 of the register 7, registering the group of sets of the pulse wave signal having the aforedescribed shape. The pulse diagnostician, using a visually perceived shape of the pulse wave signal in keeping with the character of changes in the parameters established, can define the condition of internal organs and systems, however, this will require extensive training of the pulse diagnostician.

Figure 8:
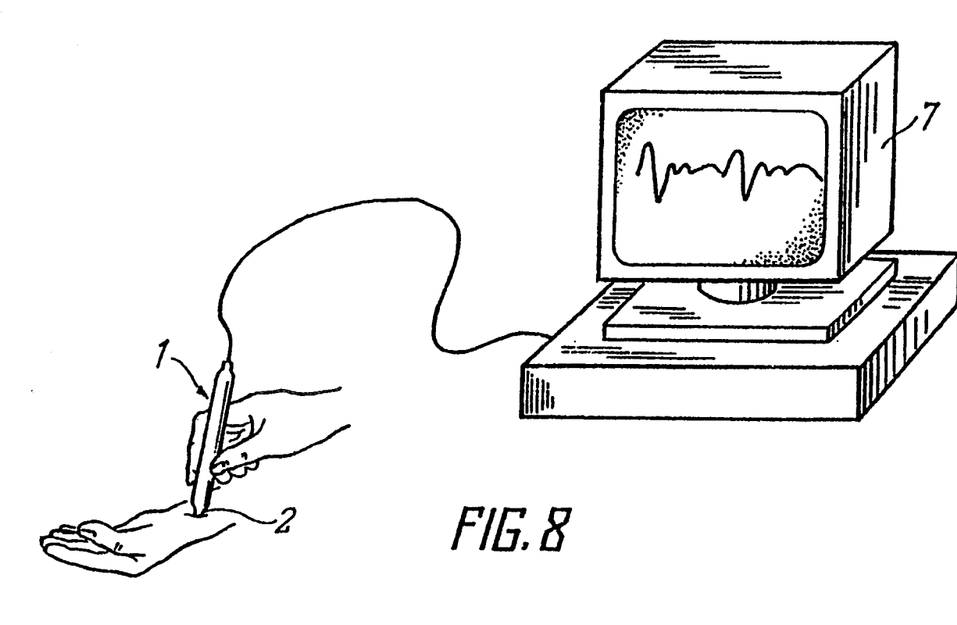
FIG. 8 shows a schematic diagram of using the pulse diagnostic device, showing arrangement of the pulse wave sensor on the patient's wrist.

It is expedient that a visually perceived shape of the pulse wave signal be used for correction of the position of the pulse wave sensor 1, both when measuring surface and deep pulses in all Cyn, Gyan and Chi points on both wrists of the patient. In this connection, the method of measuring the pulse wave using a pulse diagnostic device comprises pressing the pulse wave sensor 1 (FIG. 8) to the radial arteries in the wrists, regulating the pressure force. The doctor-pulse diagnostician manually fixes the sensor I and regulates the pressure force. In so doing, the pressure force is regulated by fixing the pulse wave sensor 1 in positions corresponding to the measurement of the surface and/or deep pulses, until the first maximum value of the maximum amplitude of the pulse wave signal appears which is visually perceived on the register 7.

The place for studying the pulse is located on the projection of the radial artery, somewhat, more proximal from the wrist joint, where there is the "beginning" and "end" of all meridians.

Above the styloid process of the radius is the Gyan pulse point, somewhat more distal there is the Cyn point and more proximal therefrom is the Chi point.

Given hereinbelow is the Table reflecting the relationship of the points and meridians.

| POINTS | LEFT HAND | | RIGHT HAND | |
|---|---|---|---|---|
| | Surface pulse | Deep pulse | Surface pulse | Deep pulse |
| CYN | Small intestines | Heart | Large intestines | Lungs |
| GYAN | Gall bladder | Liver | Stomach | Spleen |
| CHI | Urinary bladder | Kidneys | Three cavities | Pericardium |

Tabulated in the Table are positions for men. With women in the Cyn point the positions in the right and left hands are reversed: in the left hand—the large intestines (surface), the lungs (deep); in the right hand—the small intestines (surface), the heart (deep).

Under consideration in the analysis under review concerning the pulse wave signals are relationships and shape of the characteristic half-waves of each of the twelve curves.

An increase (decrease) of the maximum amplitude $a_I$ (FIG. 2) of the first characteristic half-wave I on one curve of the pulse wave signal compared to others, attests to the presence of a hyper (hypo) function of a particular organ.

Thus, an increase of the length of the first characteristic half-wave I is evidence of an internal tension of the organ in the stage of functional activity, because a larger area of the first characteristic half-wave I features a rise in the energy consumption on the execution of certain work defined by the value of the maximum amplitude $a_I$.

A decrease in the maximum amplitude $a_{II}$ of the second characteristic half-wave II is evidence of a decline in the potential energy in the organ to bring about a lower resistance and adaptation to stress factors.

A rise in the length $t_{II}$ of the second characteristic half-wave II (practically always accompanied by a decrease in the maximum amplitude $a_{II}$) attests to a possible presence of chronic diseases in a given organ.

The balance of the third and fourth characteristic half-waves III and IV features the presence inside the given organ of destructive and constructive, compensation processes, and actually shows to what extent the organ is capable of compensating and restoring the consumption of energy used to perform functions. Given approximately equal relationship of the maximum amplitudes $a_{IV}$ and $a_{III}$, one can speak about the restoration of the expended energy.

An increase in the maximum amplitude $a_{IV}$ of the fourth characteristic half-wave IV with respect to the third characteristic half-wave III is evidence of the fact that destructive processes prevail over constructive ones which, as a rule, results in a decline of reactivity and accumulation of chronic disorders.

Disappearance of the third characteristic half-wave III attests to complete termination of compensation processes which is an extreme example of the preceding case. Such relationship can also speak about the presence of dramatic changes in the organism always accompanied by greater energy consumption.

If the maximum amplitude $a_{III}$ of the third characteristic half-wave III exceeds the maximum amplitude $a_{IV}$ of the fourth characteristic half-wave IV, this shows that the organ has started restoring the potential energy reserves. These pulses are observed usually after clearance and purgation procedures, fasting, massage and the like.

Absence of the fifth characteristic half-wave V attests to a weaker regulation of the given organ on the part of the vegetative nervous system.

A pulse wave signal consists, as if, of two pans, one of which, comprising the first I, second II, third III: and fourth IV characteristic half-waves changes insignificantly in length; and the second part, limited by the fifth characteristic half-wave V which varies. Normally, the length of the fifth characteristic half-wave V is approximately equal to that of the first four characteristic half-wave I, II, III, IV. Given the length of the fifth characteristic half-wave V is less than that of the first four— this is evidence of the presence in the organism of a fever syndrome (feverish state, high temperature and the like). If the length of the fifth characteristic half-wave V exceeds that of the first four—this is evidence of the presence of a cold syndrome in the organism.

The aforementioned shape of the pulse wave carries also the information revealed through a number of other parameters, characterizing other functional disorders, e.g., presence of indurations, in particular, lithogeny as well as psychic emotional state and others.

The studies have shown a fairly high coincidence of the diagnostic conclusions obtained with the help of the claimed pulse diagnostic device not only with Oriental medicine, but also with the dam available to the Western medicine. Patients having the known diagnoses or those examined by Western medicine methods were examined at the same time as regards their pulse rate and beats. As a result, interrelationships have been observed between the data of computer-aided pulse diagnostics and Western medicine. Major difference lies only in the accent, since in pulse diagnostics the main emphasis is placed on the functional condition, while organ changes are secondary for analysis. Thus, it becomes possible to collate and compare the conceptions of Western and Oriental medicine about the condition of organs and respective functional systems.

Given below are the clinical data obtained from the examination of patients using the pulse diagnostic device of the invention.

EXAMPLE 1

A male patient, birthdate 1954. Diagnosis: chronic colitis.

Complaints: bad stools, dull headaches, frequent colds, poor appetite.

Examination: a pulse diagram of the large intestines shows excessive functional activity, i.e., $a_I$ is above the norm; internal disbalance of the third and fourth characteristic half-waves, at which $a_{IV} > a_{III}$, the condition, interpreted in the Oriental medicine as "fever", that is defined by the parameter $T/t_V$.

The spleen pulse diagram shows a decline in functional activity and reactivity, i.e., $a_I$ and $a_{II}$ are below the norm; the internal disbalance of the third and fourth characteristic half-waves, at which $a_{IV} > a_{III}$, which fact characterizes a deviation of the functional condition of the spleen from the norms /NA/ and may reduce immunity, because the spleen function is closely related to the function of the lymphatic system.

Thus, the patient's condition coincides with the data of pulse diagnostics.

EXAMPLE 2

A male patient, birthday 1956. Diagnosis: ulcer of the stomach, cholecystitis, herniotomy in 1975.

Complaints: periodic violent pains is the epigastric region, nausea, heartburn, bitter taste in the mouth in the morning, higher nervous excitability.

Examination: excessive functional activity of the stomach is observed on the gastric pulse diagram, i.e., $a_I$ is above the norm, and excessive reactivity, i.e., $a_{II}$ exceeds the norm; the presence of internal disbalance of the third and fourth characteristic half-waves, at which $a_{IV} > a_{III}$, featuring the availability of internal pathology. Excessive functional activity and reactivity are observed in the gall bladder pulse diagram, i.e., $a_I$ and $a_{II}$ exceed the norm; internal disbalance of the third and fourth characteristic half-waves, i.e., $a_{IV} > a_{III}$. Excessive functional activity, i.e., $a_I$ exceeds the norm, is observed in the pulse diagram of the three cavities.

Thus, the data of pulse diagnostics corroborate the diagnosis fairly accurately and in detail.

EXAMPLE 3

A female patient, birthday 1933. Diagnosis: tachycardia, vegetovascular dystonia, dyskinesia of the large intestine, hemorrhoids, varicosis, chronic laryngitis, cervical and thoracolumbar osteochondrosis, arthrosis of knee and femur joints with secondary spondylosis, insomnia.

Complaints: insomnia, pains in the vertebral column, pains in the joints during walk, dyspnea, bad stools, memory failure.

Examination: the liver pulse diagram shows a marked decline in the liver functional activity and reactivity, i.e., $a_I$ and $a_{II}$ are below the norm, which fact attests to chronic disorders in the liver functions and may, according to the conceptions of Oriental medicine, bring about henorrhoids, varicoses and arthtosis. The large intestine pulse diagram shows an appreciable decline in the functional activity and reactivity of the large intestines, i.e., $a_I$ and $a_{II}$ are below the norm which fact is evidence of dyskinesia of the large intestine. The lungs pulse diagram also shows a marked decline in the functional activity and reactivity of the lungs, i.e., $a_I$ and $a_{II}$ are below the norm; internal disbalance of the third and fourth characteristic half-waves, i.e., $a_{IV} > a_{III}$ which is doubtless the result of chronic laryngitis. The pulse in all positions is rapid (pulses frequent/due to tachycardia). The pericardium pulse diagram shows a decline in the pericardium activity, i.e., $a_I$ is below the norm, and also $t_1$ is below the norm (weak tense pulse), which manifests itself in vegetovascular dystonia.

Thus, the data of examination coincide as a whole and confirm the data of diagnosis.

EXAMPLE 4

A male patient, birthday 1945. Diagnosis: ischemia of the heart, cholecystitis, chronic bronchitis, Stage I hypertension.

Complaints: cough, dyspnea, periodic headaches, bad stools, pains in the region below ribs.

Examination: the heart pulse diagram shows a marked decline in functional activity and reactivity of the heart, i.e., $a_I$ and $a_{II}$ are below the norm; internal disbalance of the third and fourth characteristic half-waves, i.e., $a_{IV} > a_{III}$, the fifth characteristic half-wave is reduced to a straight line. The pulse diagrams of the gall bladder, liver, stomach and spleen feature excessive functional activity and reactivity, i.e., $a_I$ and $a_{II}$ are above the norm; internal disbalance of the third and fourth characteristic half-waves at which $a_{IV} > a_{III}$, which symptomatically may be expressed by pains in the region below the ribs. The pulse diagram of the lungs shows a decline in the lungs functional activity, i.e., $a_I$ is below the norm, the second characteristic half-wave is actually degenerated, i.e., $a_{II}$ is markedly below the norm which shows an old functional disorder (chronic bronchitis). The pulse diagram of the large intestines shows a drop in its functional activity, i.e., $a_I$ is below the norm. The pulse diagram of the pericardium shows excessive functional activity, i.e., $a_I$ is above the norm to reflect overstress of the vascular system.

We claim:

1. A pulse diagnostic device, comprising:
at least one pulse wave sensor, said at least one pulse wave sensor having an amplitude-frequency response and adapted to be mounted on the inside of the wrist in the Cyn, Gyan and Chi points on an arterial artery for generating a pulse wave signal;
means for correcting the amplitude-frequency response of said pulse wave sensor to obtain a pulse wave signal of a prescribed shape containing a set of characteristic half-waves;
a pulse wave signal processing unit coupled to the pulse wave sensor, said pulse wave signal processing unit processing the set of characteristic half-waves, said pulse wave signal processing unit incorporating:
an amplifier, having an input serving as said input of said pulse wave signal processing unit, and an output;
an analog-to-digital converter, connected to said output of said amplifier;
an analyzer of the pulse wave signal shape, said analyzer comparing amplitudinal and temporal relationships between the characteristic half-waves, said analyzer having an input, connected to said output of said analog-to-digital converter, and having an output serving as said output of said pulse wave signal processing unit; and
a register, having a first input connected to said output of said pulse wave signal processing unit, said register registering the set of characteristic half-waves.

2. A pulse diagnostic device as claimed in claim 1, wherein said means for correcting the amplitude-frequency response of said pulse wave sensor forms the pulse wave signal wherein the signal contains first, second, third, fourth and fifth characteristic sinusoidal half-waves, following one after another, the first characteristic half-wave being a positive characteristic half-wave, the second characteristic half-wave being a negative characteristic half-wave whose amplitude is substantially equal to the amplitude of the first characteristic half-wave, the third and fourth characteristic half-waves being positive characteristic half-waves of substantially the same amplitude, which is less than the amplitude of the first characteristic half-wave, and the fifth characteristic half-wave being a positive characteristic half-wave whose amplitude is no more than the amplitude of the third and fourth characteristic half-waves and whose length is basically equal to the total length of the first, second, third and fourth characteristic half-waves.

3. A pulse diagnostic device as claimed in claim 2, comprising:
a microphone, serving as said pulse wave sensor;
a chamber, serving as said means for correcting the amplitude-frequency responses of said pulse wave sensor which is arranged in front of said microphone;
working medium filling said chamber.

4. A pulse diagnostic device, as claimed in claim 3, wherein said chamber is open at a side of entry of an acoustic wave, air serving as said working medium.

5. A pulse diagnostic device, as claimed in claims 2, 3, or 4 wherein said analyzer of the pulse wave signal shape incorporates:
a memory unit, having an input serving as said input of said analyzer, and an output;
a unit assigning a separate set of said characteristic half-waves with maximum energy and revealing therein of characteristic half-waves, said assigning unit having an input and output connected by said assigning unit input to said output of said memory unit;
a calculator of parameters which calculates maximum amplitudes and lengths of the first and second characteristic half-waves, calculates maximum amplitudes of the third and fourth characteristic half-waves, determines a first relationship between the maximum amplitudes of the fourth and third characteristic half-waves and determines a second relationship between the lengths of the set of characteristic half-waves and the fifth characteristic half-wave, said calculator having an input and output, said calculator input connected to said output of said unit assigning a separate set;

a comparator unit, having first and second inputs and an output, connected by the first input to said output of said calculator of parameters;

a set-point device having an output, connected to the second input of said comparator unit, said output serving as said output of said analyzer.

6. A pulse diagnostic device as claimed in claim 5, comprising:

said register having a second register input;

said amplifier of said processing unit, connected by said amplifier output to the second register input of said registèr, the register registering a group of sets of the pulse wave signal.

7. A pulse diagnostic device according to claim 1 wherein the means for correcting the amplitude-frequency response comprises an acoustic filter with a bandwidth approximately between 5 and 135 Hz.

8. A method for measuring a pulse wave by means of a pulse diagnostic device, comprising a pulse wave sensor and a register, electrically connected to said pulse wave sensor, including the following operations:

pressing the pulse wave sensor to the wrists in the Cyn, Gyan and Chi points, reflecting the condition of internal organs and systems effected by the force created by hand;

regulation of the force of said pressure to install the pulse wave sensor in the positions corresponding to measurement of the surface and/or deep pulses; said regulation effected until a first maximum value of the maximum amplitude of the pulse wave signal is visually perceived in the register; and correcting the amplitude response of the pulse wave signal from the pulse wave sensor to contain multiple characteristic half-waves.

9. A method according to claim 8 including comparing the amplitude and duration of at least one characteristic half-wave with the amplitude and duration of at least one of the remaining characteristic half waves for diagnosis of organ and systems failure.

* * * * *